United States Patent
Leighton et al.

(10) Patent No.: US 9,629,920 B2
(45) Date of Patent: Apr. 25, 2017

(54) METHODS AND COMPOSITIONS FOR STABLE LIQUID DRUG FORMULATIONS

(75) Inventors: Harry J. Leighton, Rockport, ME (US); Crist J. Frangakis, Chapel Hill, NC (US)

(73) Assignee: Exodos Life Sciences Limited Partnership, Chapel Hill, NC (US)

( * ) Notice: Subject to any disclaimer, the term of this patent is extended or adjusted under 35 U.S.C. 154(b) by 207 days.

(21) Appl. No.: 13/517,024

(22) PCT Filed: Dec. 17, 2010

(86) PCT No.: PCT/US2010/061135
§ 371 (c)(1),
(2), (4) Date: Dec. 6, 2012

(87) PCT Pub. No.: WO2011/075691
PCT Pub. Date: Jun. 23, 2011

(65) Prior Publication Data
US 2013/0071412 A1 Mar. 21, 2013

Related U.S. Application Data

(60) Provisional application No. 61/287,988, filed on Dec. 18, 2009.

(51) Int. Cl.
| | | |
|---|---|---|
| *A61K 47/48* | (2006.01) | |
| *A61K 9/00* | (2006.01) | |
| *A61K 47/42* | (2006.01) | |
| *A61K 9/16* | (2006.01) | |
| *A61K 31/4468* | (2006.01) | |
| *A61K 45/06* | (2006.01) | |
| *A61K 9/50* | (2006.01) | |
| *A61K 31/192* | (2006.01) | |

(52) U.S. Cl.
CPC ...... *A61K 47/48246* (2013.01); *A61K 9/0095* (2013.01); *A61K 9/1658* (2013.01); *A61K 9/5089* (2013.01); *A61K 31/192* (2013.01); *A61K 31/4468* (2013.01); *A61K 45/06* (2013.01); *A61K 47/42* (2013.01); *A61K 47/483* (2013.01); *A61K 47/48284* (2013.01); *A61K 47/48292* (2013.01); *A61K 47/48369* (2013.01)

(58) Field of Classification Search
None
See application file for complete search history.

(56) References Cited

U.S. PATENT DOCUMENTS

| | | |
|---|---|---|
| 2003/0064107 A1 | 4/2003 | Yu et al. |
| 2005/0282734 A1* | 12/2005 | Kadima ............... A61K 47/42 |
| | | 514/15.2 |
| 2008/0160095 A1 | 7/2008 | Desai et al. |
| 2008/0306245 A1 | 12/2008 | Sinn et al. |
| 2009/0176884 A1 | 7/2009 | Dickerson et al. |

FOREIGN PATENT DOCUMENTS

| | | |
|---|---|---|
| CN | 1270529 A | 10/2000 |
| EA | 200602183 A1 | 6/2007 |
| EA | 200801323 A1 | 10/2009 |
| EP | 0326618 A1 | 8/1989 |
| EP | 2359859 A1 | 8/2011 |
| JP | 61-271226 A | 12/1986 |
| JP | S63-215640 A | 9/1988 |
| JP | S63-215640 A | 8/1989 |
| JP | 05-238947 A | 9/1993 |
| JP | 11-258236 A | 9/1999 |
| JP | 2006-524632 A | 11/2006 |
| RU | 2205662 C2 | 6/2003 |
| RU | 2352583 C2 | 4/2009 |
| WO | WO-98/51349 A1 | 11/1998 |
| WO | WO-99/13914 A1 | 3/1999 |
| WO | WO-2005/047337 A1 | 5/2005 |
| WO | WO-2005/118642 A | 12/2005 |
| WO | WO-2011/075654 A1 | 6/2011 |
| WO | WO-2011/075655 A1 | 6/2011 |
| WO | WO-2011/075688 A1 | 6/2011 |

OTHER PUBLICATIONS

Fomon, Samuel, Infant Feeding in the 20th Century: Formula and Beikost. Journal of Nutrition 131:409S-420S, 2001.*
Fomon, Infant feeding in the 20th century: formula and beikost. J Nutr. 131(2):409S-20S, 2001.*
U.S. Appl. No. 13/517,008, filed Nov. 27, 2012, Leighton et al.
U.S. Appl. No. 13/517,010, filed Nov. 1, 2012, Frangakis et al.
U.S. Appl. No. 13/517,016, filed Jan. 8, 2013, Leighton et al.

(Continued)

*Primary Examiner* — Ruixiang Li
(74) *Attorney, Agent, or Firm* — Clark & Elbing LLP

(57) ABSTRACT

The invention features a powdered composition including a pharmaceutically active compound and a protein or a hydrolyzed protein. In particular, the powdered composition forms a stable solution or dispersion suitable for oral administration in which the protein or the hydrolyzed protein is bound to the pharmaceutically active compound. The invention also provides a method of administering the composition, such as to a patient with dysphasia; liquid or semi-solid formulations of the composition; methods for preparing the composition; and kits including the composition.

24 Claims, 4 Drawing Sheets

(56) References Cited

OTHER PUBLICATIONS

International Search Report and Written Opinion for International Application No. PCT/US2010/061135, mailed Feb. 28, 2011 (11 pages).
Reddy et al., "Formulation and evaluation of oral and transdermal preparations of flurbiprofen and piroxicam incorporated with different carriers," Drug Dev Ind Pharm. 19(7):843-52 (1993).
Imai et al., "Enhancement of dissolution and absorption of mefenamic acid by egg albumin," J Pharm Sci. 80(5):484-7 (1991).
Kolosova et al., "Development of an enzyme-linked immunosorbent assay for gentamicin in human blood serum." Fresenius J Anal Chem. 361:329-30 (1998).
English translation of the Notice of Reasons for Rejection for Japanese Patent Application No. 2012-544920, mailed Aug. 19, 2014 (5 pages).
English translation of the Official Action for Russian Application No. 2012130391, dated Dec. 22, 2014 (4 pages).
Examination Report for Australian Patent Application No. 2010330750, issued Sep. 30, 2014 (3 pages).
Extended European Search Report for European Application No. EP10838322, dated Dec. 18, 2014 (6 pages).
English translation of Notice of Reasons for Rejection for Japanese Patent Application No. 2012-544920, mailed Jun. 9, 2015 (8 pages).
"Prednisone (by mouth)," National Library of Medicine—PubMed Health, <https://www.ncbi.nlm.nih.gov/pubmedhealth/PMHT0011828/>, accessed Oct. 21, 2016 (2 pages).
Actos (pioglitazone). Deerfield, IL: Takeda Pharmaceuticals America, Inc., 2013 (42 pages).
Aricept (donepezil hydrochloride). Woodcliff Lake, NJ: Eisai Inc., 2015 (28 pages).
Diovan (valsartan). East Hanover, NJ: Novartis Pharmaceuticals Corporation, 2015 (19 pages).
Lipitor (atorvastatin calcium). New York, NY: Pfizer Inc, 2012 (24 pages).
Lopressor (metoprolol). East Hanover, NJ: Novartis Pharmaceuticals Corporation, 2012 (16 pages).
Mayo Clinic Staff, "Prednisone and other corticosteroids," <http://www.mayoclinic.org/steroids/art-20045692>, accessed Oct. 21, 2016 (3 pages).
Nexium (esomeprazole magnesium). Wilmington, DE: AstraZeneca Pharmaceuticals, 2014 (33 pages).
Norvasc (amlodipine besylate). New York, NY: Pfizer Inc, 2015 (15 pages).
Office Action for Japanese Application No. 2015-201055, mailed Sep. 6, 2016 (5 pages).
Prevacid (lansoprazole). Deerfield, IL: Takeda Pharmaceuticals America, Inc., 2015 (39 pages).
Prilosec (omeprazole). Wilmington, DE: AstraZeneca Pharmaceuticals LP, 2014 (48 pages).
Procardia (nifedipine). New York, NY: Pfizer Inc, 2014 (12 pages).
Zyprexa (olanzapine). Indianapolis, IN: Eli Lilly and Company, 2009 (41 pages).

* cited by examiner

METHODS AND COMPOSITIONS FOR STABLE LIQUID DRUG FORMULATIONS

CROSS REFERENCE TO RELATED APPLICATIONS

This application claims priority under 35 U.S.C. §371 from International Application No. PCT/US2010/061135, filed Dec. 17, 2010, which claims priority under 35 U.S.C. §119 from U.S. Provisional Application No. 61/287,988, filed Dec. 18, 2009.

BACKGROUND OF THE INVENTION

The present invention relates to liquid formulations of pharmaceutically active compounds. In particular, the invention relates to liquid formulations prepared by admixing a liquid with a powdered composition. The resulting liquid formulation is a stable solution or dispersion in which the protein is bound to the pharmaceutically active compound. The protein can be full length or various hydrolyzed fragments thereof. Also provided herein are methods for preparing the powdered composition, as well as kits for preparing the liquid formulation.

Though only encompassing about 13% of the general population, elderly patients account for around 33% of all prescribed medications. The average ambulatory senior takes almost six medications simultaneously, while a nursing home patient may take seven to ten medications. In general, a larger pill (e.g., a capsule, a gel cap, or a tablet) results in greater difficulty in swallowing the medication. For the elderly, swallowing medications can be difficult or painful, a condition commonly referred to as dysphagia, which can lead to low compliance by the patient. Dysphagia is also associated with several chronic diseases, including neurodegenerative diseases (e.g., Alzheimer's disease, Parkinson's disease, etc.), psychiatric diseases, metabolic diseases, and endocrine diseases. It can also be a problem for patients receiving radiation or chemotherapy.

For patients suffering from dysphagia who are on medication, it is common practice for the patient or healthcare professional to crush the medication and mix it into a favorite liquid or soft food, such as applesauce, for consistency and taste masking. In some instances, multiple medications may be crushed and then mixed together within the patient's food or drink. While compliance may be increased by this practice, dose strength, drug stability, and pharmacokinetics are compromised, adversely affecting the efficacy of the medication.

Liquid formulations have been widely used for pediatric medications to provide for easier administration. These formulations are well known in the art and are exemplified by, for example, various antibiotics, such as amoxicillin, augmentin, and gatifloxacin; antiasthmatics, such as zafirlukast (Accolate®); and antivirals, such as zidovudine, lamivudine, stavudine, and abacavir. By contrast, little systematic effort has been made to develop liquid formulations for geriatric patients or other adult patients with swallowing difficulties. In practice, a compounding pharmacist may attempt to make a liquid formulation for an older patient, but no consistent and reliable method has been developed for all drug products.

The above-mentioned problems lead to sub-optimal and/or erratic dosing, which may affect disease progression and lead to an increase in long term health care. Thus, there is a need for stable and effective liquid formulations for delivering a variety of pharmaceutical agents.

SUMMARY OF THE INVENTION

In a first aspect, the invention features a method of administering a pharmaceutically active compound to a patient, the method including the steps of: providing a powdered composition including a pharmaceutically active compound and a protein or a hydrolyzed protein, where the protein or the hydrolyzed protein is from 500 Da to 10,000,000 Da; mixing the powdered composition with a liquid or semi-solid to form a stable solution or dispersion in which the protein or the hydrolyzed protein is bound to the pharmaceutically active compound; and orally administering the solution or dispersion to the patient.

In one embodiment of the first aspect, the method includes the pharmaceutically active compound and the protein or the hydrolyzed protein present in a ratio of from 1:1 to 1:1,000. In another embodiment, the composition includes 1% to 30% (w/w) the pharmaceutically active compound and 90% to 99% (w/w) of the protein or the hydrolyzed protein. In yet another embodiment, the protein or the hydrolyzed protein is from 500 Da to 1,000,000 Da.

In another embodiment of the first aspect, the invention features a method where the composition is denatured or partially denatured. In one embodiment, the size of the powder is from 1 to 100 mesh. In yet another embodiment, the invention features a method where the liquid is water or an aqueous solution.

In an embodiment of the first aspect, the invention features a method where the viscosity of the dispersion is from 1 cP to 450 cP. In another embodiment, the viscosity of the dispersion is from 50,000 cP to 200,000 cP.

In a further embodiment of the first aspect, the pharmaceutically active compound is less than 500 Da.

In a particular embodiment, the pharmaceutically active compound is one or more of a 5-$HT_{1A}$ receptor agonist, a 5-$HT_2$ receptor antagonist, an α-adrenergic receptor agonist, an α-adrenergic receptor antagonist, a β-adrenergic receptor agonist, a β-adrenergic receptor antagonist, an acetylcholinesterase inhibitor, an anesthetic, an angiotensin receptor antagonist, an angiotensin converting enzyme inhibitor, an antibiotic, an anticholinergic agent, an anticoagulant, an anticonvulsant, an antidepressant, an antidiabetic agent, an antifungal agent, an antiinflammatory agent, an antihistamine, an antipsychotic agent, an antiplatelet agent, an antiviral agent, an anxiolytic agent, a cholesterol-lowering drug, a dopamine agonist, a dopamine antagonist, an eicosanoid inhibitor, a glucocorticoid, an ion channel blocking agent, a monoamine oxidase B inhibitor, an N-methyl d-aspartate receptor antagonist, a norepinephrine reuptake inhibitor, a prostaglandin, a proton pump inhibitor, a renin antagonist, a serotonergic, a steroidal anti-inflammatory agent, a tricyclic, a thromboxane A2 agonist, a triptan, a vasodilator, or a nutraceutical.

In another embodiment of the first aspect, the invention features a method where the protein or the hydrolyzed protein is one or more of gelatin (e.g., type A gelatin and type B gelatin), casein, whey protein (e.g., alpha-lactalbumin, beta lactoglobulin, bovine serum albumin, a glycomacropeptide, immunoglobulin, lactoferrin, and lactoperoxidase), albumin (e.g., bovine serum albumin and human serum albumin), or soy protein (e.g., β-conglycinin and glycinin). In a further embodiment, the protein or the hydrolyzed protein includes from 70% to 95% (w/w) of whey protein or from 80% to 95% (w/w) of casein.

In a further embodiment of the first aspect, the invention features a method where the composition further includes one or more agents selected from the group consisting of an absorption enhancing agent (e.g., achitosan, type A gelatin, and type B gelatin), an antimicrobial (e.g., methylparaben, propylparaben, sodium benzoate, propyl benzoate, sodium sorbate, potassium sorbate, and calcium sorbate), an antioxidant (e.g., methylparaben, propylparaben, sodium benzoate, propyl benzoate, sodium sorbate, potassium sorbate, and calcium sorbate), a buffering agent (e.g., citric acid, malic acid, tartaric acid, phosphoric acid, and pharmaceutically acceptable salts thereof), a colorant, a dispersing agent (e.g, polyvinylpyrrolidine, an alkyhydroxy cellulose, a dextrin, a cyclodextrin, and a polyhydroxyalcohol), a flavoring agent, a preservative (e.g., ethylenediaminetetraacetic acid and a 4-hydroxy benzoic ester), a solubilizing agent (e.g., 200 Da to 1000 Da polyethylene glycol, sorbitol, a glycol polyol, and dipropylene glycol polyethylene), a stabilizing agent (e.g., glycerin, pentaerythritol, and sodium alginate), a surfactant (e.g., polyoxylglyceride, a caprylate, a laurate, an oleate, a monoethyl ether, a sorbitan-based nonionic surfactant, a polyoxyethylene sorbitan-based surfactant, an emulsifier blend, and tocopherol polyethyleneglycol 1000 succinate), a sweetener (e.g., L-aspartylyphenylalanine methyl ester, a stevia saccharin salt, a cyclamate salt, acefulfam-K, aspartame, sucralose, a glycyrrhizanate, glucose, xylose, ribose, mannose, fructose, dextrose, sorbitol, mannitol, thymidine, and monellin), a taste masking agent (e.g., sodium alginate, xanthum gum, carageenan, hydroxypropylmethyl cellulose, methyl cellulose, microcrystalline cellulose, or sodium carboxy methyl cellulose), a viscosity controlling agent (e.g., gelatin, alginic acid, agarose, agar, carrageenan, xanthan gum, locust bean gum, guar gum, tragacanth, gum karaya, natural gum, methyl cellulose, glucomannan, galactomannan, and gulaman), and a vitamin. In a further embodiment, the amount of the buffering agent results in the dispersion having a pH from 6 to 8. In yet a further embodiment, the pH is from 6.8 to 7.2.

In a second aspect, the invention features a powdered composition including a pharmaceutically active compound, and a protein or a hydrolyzed protein of greater than 500 kDa, where the composition when admixed with a liquid or semi-solid forms a stable solution or dispersion suitable for oral administration in which the protein or the hydrolyzed protein is bound to the pharmaceutically active compound.

In one embodiment of the second aspect, the pharmaceutically active compound and the protein or the hydrolyzed protein are present in a ratio of from 1:1 to 1:1000.

In another embodiment of the second aspect, the composition includes 1% to 30% (w/w) the pharmaceutically active compound and 90% to 99% (w/w) of the protein or the hydrolyzed protein. In a further embodiment, the composition is denatured or partially denatured. In yet another embodiment, the size of the powder is from 1 to 100 mesh. In one particular embodiment, the liquid is water or an aqueous solution.

In one embodiment of the second aspect, the viscosity of the dispersion is from 1 to 450 cP. In another embodiment, the viscosity of the dispersion is from 50,000 cP to 200,000 cP.

In one embodiment of the second aspect, the invention features a powdered composition where the pharmaceutically active compound is greater than 500 Da. In a further embodiment, the pharmaceutically active compound is one or more a 5-HT$_{1A}$ receptor agonist, a 5-HT$_2$ receptor antagonist, an α-adrenergic receptor agonist, an α-adrenergic receptor antagonist, a β-adrenergic receptor agonist, a β-adrenergic receptor antagonist, an acetylcholinesterase inhibitor, an anesthetic, an angiotensin receptor antagonist, an angiotensin converting enzyme inhibitor, an antibiotic, an anticholinergic agent, an anticoagulant, an anticonvulsant, an antidepressant, an antidiabetic agent, an antifungal agent, an antiinflammatory agent, an antihistamine, an antipsychotic agent, an antiplatelet agent, an antiviral agent, an anxiolytic agent, a cholesterol-lowering drug, a dopamine agonist, a dopamine antagonist, an eicosanoid inhibitor, a glucocorticoid, an ion channel blocking agent, a monoamine oxidase B inhibitor, an N-methyl d-aspartate receptor antagonist, a norepinephrine reuptake inhibitor, a prostaglandin, a proton pump inhibitor, a renin antagonist, a serotonergic, a steroidal anti-inflammatory agent, a tricyclic, a thromboxane A2 agonist, a triptan, a vasodilator, or a nutraceutical.

In another embodiment of the second aspect, the protein or the hydrolyzed protein is one or more of gelatin (e.g., type A gelatin and type B gelatin), casein, whey protein (e.g., alpha-lactalbumin, beta lactoglobulin, bovine serum albumin, a glycomacropcptide, immunoglobulin, lactoferrin, and lactoperoxidase), albumin (e.g., bovine serum albumin and human serum albumin), or soy protein (e.g., β-conglycinin and glycinin). In a further embodiment, the protein or the hydrolyzed protein includes from 70% to 95% (w/w) of whey protein or from 80% to 95% (w/w) of casein.

In a further embodiment of the second aspect, the invention features a composition further including one or more agents selected from the group consisting of an absorption enhancing agent (e.g., achitosan, type A gelatin, and type B gelatin), an antimicrobial (e.g., methylparaben, propylparaben, sodium benzoate, propyl benzoate, sodium sorbate, potassium sorbate, and calcium sorbate), an antioxidant (e.g., methylparaben, propylparaben, sodium benzoate, propyl benzoate, sodium sorbate, potassium sorbate, and calcium sorbate), a buffering agent (e.g., citric acid, malic acid, tartaric acid, phosphoric acid, and pharmaceutically acceptable salts thereof), a colorant, a dispersing agent (e.g, polyvinylpyrrolidine, an alkyhydroxy cellulose, a dextrin, a cyclodextrin, and a polyhydroxyalcohol), a flavoring agent, a preservative (e.g., ethylenediaminetetraacetic acid and a 4-hydroxy benzoic ester), a solubilizing agent (e.g., 200 Da to 1000 Da polyethylene glycol, sorbitol, a glycol polyol, and dipropylene glycol polyethylene), a stabilizing agent (e.g., glycerin, pentaerythritol, and sodium alginate), a surfactant (e.g., polyoxylglyceride, a caprylate, a laurate, an oleate, a monoethyl ether, a sorbitan-based nonionic surfactant, a polyoxyethylene sorbitan-based surfactant, an emulsifier blend, and tocopherol polyethyleneglycol 1000 succinate), a sweetener (e.g., L-aspartylyphenylalanine methyl ester, a stevia saccharin salt, a cyclamate salt, acefulfam-K, aspartame, sucralose, a glycyrrhizanate, glucose, xylose, ribose, mannose, fructose, dextrose, sorbitol, mannitol, thymidine, and monellin), a taste masking agent (e.g., sodium alginate, xanthum gum, carageenan, hydroxypropylmethyl cellulose, methyl cellulose, microcrystalline cellulose, or sodium carboxy methyl cellulose), a viscosity controlling agent (e.g., gelatin, alginic acid, agarose, agar, carrageenan, xanthan gum, locust bean gum, guar gum, tragacanth, gum karaya, natural gum, methyl cellulose, glucomannan, galactomannan, and gulaman), and a vitamin. In a further embodiment, the amount of the buffering agent results in the dispersion having a pH from 6 to 8. In yet a further embodiment, the pH is from 6.8 to 7.2.

In a third aspect, the invention features a liquid or semi-solid formulation prepared by mixing the powdered composition described herein with a liquid or semi-solid. In one embodiment, the liquid is an aqueous solution. In another embodiment, pH is between 6 and 8 (e.g., between 6.8 and 7.2). In yet another embodiment, the viscosity is from 1 cP to 450 cP or from 50,000 cP to 200,000 cP.

In a fourth aspect, the invention features a method for preparing a powdered composition including: dispersing a protein or a hydrolyzed protein in an aqueous solution at a first temperature ranging from 10° C. to 50° C. to form a protein mixture; adding an effective amount of a pharmaceutically active compound to the protein mixture; before or after the compound has been added to the protein mixture, heating the protein mixture to a second temperature ranging from 23° C. to 60° C., where the amount of the protein or the hydrolyzed protein is in excess of the effective amount of the compound; cooling the mixture to a third temperature ranging from 5° C. to 23° C.; and separating the mixture from the aqueous solution to obtain the powdered composition.

In one embodiment of the fourth aspect, the protein or the hydrolyzed protein is one or more of gelatin, casein, whey protein, albumin, or soy protein. In another embodiment, the aqueous solution is water or a buffer. In a further embodiment, the buffer has a pH between 6 and 8.

In another embodiment of the fourth aspect, the method includes an aqueous solution that further includes one or more agents selected from the group consisting of an absorption enhancing agent, an antimicrobial, an antioxidant, a buffering agent, a colorant, a dispersing agent, a flavoring agent, a preservative, a solubilizing agent, a stabilizing agent, a surfactant, a sweetener, a taste masking agent, a viscosity controlling agent, and a vitamin.

In one embodiment of the fourth aspect, the first temperature range is from 20° C. to 25° C. In another embodiment, the second temperature range is from 25° C. to 37° C. In yet another embodiment, the third temperature range is from 23° C. to 37° C.

In a fifth aspect, the invention features a kit including a powdered composition that can be admixed with a liquid to form a stable solution or dispersion suitable for oral administration to a patient, said composition including: 1% to 30% (w/w) of a pharmaceutically active compound and 70% to 99% (w/w) of a protein or a hydrolyzed protein of greater than 500 kDa, where said compound is bound to said protein; a liquid; and instructions on admixing the powdered composition with the liquid. In one embodiment, the powdered composition includes the pharmaceutically active compound selected from the group consisting of a 5-HT$_{1A}$ receptor agonist, a 5-HT$_2$ receptor antagonist, an α-adrenergic receptor agonist, an α-adrenergic receptor antagonist, a β-adrenergic receptor agonist, a β-adrenergic receptor antagonist, an acetylcholinesterase inhibitor, an anesthetic, an angiotensin receptor antagonist, an angiotensin converting enzyme inhibitor, an antibiotic, an anticholinergic agent, an anticoagulant, an anticonvulsant, an antidepressant, an antidiabetic agent, an antifungal agent, an antiinflammatory agent, an antihistamine, an antipsychotic agent, an antiplatelet agent, an antiviral agent, an anxiolytic agent, a cholesterol-lowering drug, a dopamine agonist, a dopamine antagonist, an eicosanoid inhibitor, a glucocorticoid, an ion channel blocking agent, a monoamine oxidase B inhibitor, an N-methyl d-aspartate receptor antagonist, a norepinephrine reuptake inhibitor, a prostaglandin, a proton pump inhibitor, a renin antagonist, a serotonergic, a steroidal anti-inflammatory agent, a tricyclic, a thromboxane A2 agonist, a triptan, a vasodilator, or a nutraceutical. In another embodiment, the powdered composition includes the protein or the hydrolyzed protein selected from the group consisting of gelatin, casein, whey protein, albumin, and soy protein.

In yet another embodiment of the fifth aspect, the liquid includes one or more agents selected from the group consisting of an absorption enhancing agent, an antimicrobial, an antioxidant, a buffering agent, a colorant, a dispersing agent, a flavoring agent, a preservative, a solubilizing agent, a stabilizing agent, a surfactant, a sweetener, a taste masking agent, a viscosity controlling agent, and a vitamin.

Definitions

As used herein, "bound" and "binding" refers to a non-covalent or a covalent interaction that holds two molecules together. For example, two such molecules could be a pharmaceutically active compound and a protein. Non-covalent interactions include, but are not limited to, hydrogen bonding, ionic interactions among charged groups, electrostatic binding, van der Waals interactions, hydrophobic interactions among non-polar groups, lipophobic interactions, and LogP-based attractions.

By "complex" is meant a pharmaceutically compound bound to a full length protein or a hydrolyzed protein.

By "drug class protein" is meant a protein that binds a class of pharmaceutically active compounds.

As used herein, the phrase "an effective amount of a pharmaceutically active compound" refers to an available amount of one or more compounds in a liquid formulation that will provide a therapeutic benefit to a patient.

By "pharmacophore" is meant a functional group present in a pharmaceutically active compound that imparts its therapeutic function.

By "stable dispersion" is meant a dispersion that stabilizes a pharmaceutically active compound that is admixed in a liquid or in a semi-solid food product.

By "patient" is meant a mammal, including, but not limited to, a human or non-human mammal.

By "hydrolyzed protein" is meant a protein fragment formed by breaking of one or more peptide bonds in a full length protein.

The recitation herein of numerical ranges by endpoints is intended to include all numbers subsumed within that range (e.g., a recitation of 1 to 5 includes 1, 1.5, 2, 2.75, 3, 3.80, 4, and 5).

As used herein, "a" or "an" means "at least one" or "one or more" unless otherwise indicated. In addition, the singular forms "a", "an", and "the" include plural referents unless the context clearly dictates otherwise. Thus, for example, reference to a composition containing "a compound" includes a mixture of two or more compounds.

Other features and advantages of the invention will be apparent from the following Detailed Description and from the claims.

DETAILED DESCRIPTION

Figure 1A:
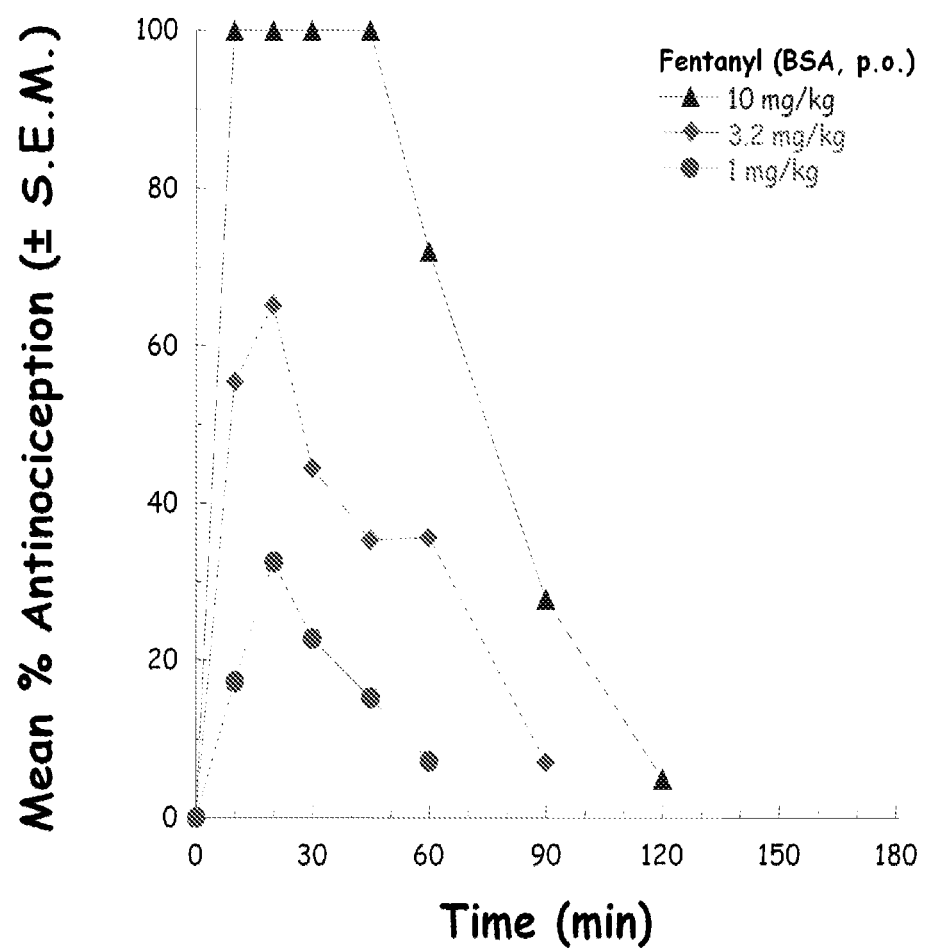
FIG. 1A is a graph showing antinociception (reduction in pain) over time in mice treated with 10 mg/kg, 3.2 mg/kg, or 1 mg/kg fentanyl formulated in water.

This invention features a powdered composition that contains a complex of a pharmaceutically active compound and a protein, typically a hydrolyzed protein. The powdered composition can be mixed with a liquid medium and reconstituted to provide a stable liquid solution or dispersion of the pharmaceutical agent suitable for oral consumption by a patient who has difficulty swallowing pills. The invention uses proteins as universal acceptors of organic molecules, such as pharmaceutically active compounds, with molecular weights preferably under 500 Daltons (Da). The invention can be applied to virtually all pharmaceutically active compounds that bind plasma protein. Surprisingly, this is true whether the compound is lipophilic, charged, or neutral. The ability of proteins to serve as such universal acceptors stems from the complicated physical chemistry and geometry of structural proteins. Plasma proteins (e.g., in humans and animals) and proteins from other sources, whether synthetic or natural, have many different binding zones that allows for tight binding of charged and non-charged molecules. Stated differently, proteins have anionic, cationic, and lipophilic sites that allow binding of all types of organic molecules and salts of organic molecules to these proteins. By using these various binding zones and sites, a complex can be formed between a pharmaceutically active compound and a protein.

Methods of Preparing the Powder Composition and Liquid Formulation

Methods are provided herein for preparing powder compositions, which can be combined with a liquid to provide a stable solution or dispersion of a pharmaceutically active compound. The method of the invention can be used to stabilize a wide variety of pharmaceutically active compounds that are generally considered to be unstable in liquid media, such as esters of drugs. Such compounds can be difficult to provide as a liquid formulation for a number of reasons. For example, the liquid media often leads to hydrolysis of the drug over time. The present invention addresses these problems by combining the drug with, for example, a hydrolyzed or partially hydrolyzed protein. The binding of the drug to the protein takes the drug out of solution and thus stabilizes the molecule from degradation. This method is applicable to all drugs, nutraceuticals, or nutrition aids that may be charged (cationic or anionic), neutral, lipophilic, or zwitterionic. It can also be applied to hydrophobic and hydrophilic drugs, all salt forms of drugs, all polymorphic forms, and other drugs not normally stable in liquid media.

Generally, the method for preparing the powdered composition includes the following steps of:

dispersing a hydrolyzed protein in an aqueous solution to form a protein mixture, wherein this step may be performed at room temperature 23° C. or at an elevated temperature that drives solubilization without denaturation and the optimal temperature can be determined for each protein using known methods;

adding an effective amount of a pharmaceutically active compound to the protein mixture and heating the mixture to bind the drug to the protein, wherein the amount of the protein is typically in excess of the effective amount of the compound, wherein this step is performed at an optimal temperature for solubilization (e.g., between 23° C. and 60° C.);

cooling the mixture (e.g., to a temperature between 5° C. and 23° C.); and separating the mixture from the aqueous solution to obtain the powdered composition (e.g., by filtration or centrifugation).

The method can include additional steps and modifications. For example, once separation has been completed, the resulting products may be further dried by lyophilization to a dehydrated powder. This powder can then be reconstituted in an aqueous solution with standard components, such as those excipients commonly used to optimize color, viscosity, taste characteristics, and antimicrobials.

In another example, the aqueous solution can include additional components, such as an absorption enhancing agent, an antimicrobial, an antioxidant, a buffering agent, a colorant, a dispersing agent, a flavoring agent, a preservative, a solubilizing agent, a stabilizing agent, a surfactant, a sweetener, a taste masking agent, a viscosity controlling agent, a vitamin, or any other additive or agent described herein. In addition, further steps may be included in the process to add other additives or agents.

Examples of other additive or agents that may be used in the compositions of the invention include, but are not limited to, absorption enhancing agents, adjuvants, antimicrobials, antioxidants, buffering agents, chelating agents, demulcents, demulsifiers, deodorants, detergents, dispersing agents, dyes emulsifiers, fillers, gelling agents, inert diluents (e.g., calcium carbonate, sodium carbonate, lactose, calcium phosphate, sodium phosphate, or kaolin), phytomedicinals, plasticizing agents, preservatives, solvents, solubilizing agents, stabilizing agents, surfactants, thickeners (e.g., xanthan gum, a fatty acid, a fatty acid salt or ester, a fatty alcohol, a modified cellulose, a modified mineral material, or a synthetic polymer), viscosity controlling agents, vitamins, or wetting agents.

Exemplary absorption enhancing agents, such as for polar molecules, include, but are not limited, to chitosan, type A gelatin, and type B gelatin.

Exemplary antimicrobials include parabens (e.g., methylparaben and propylparaben), benzoates (e.g., sodium benzoate and propyl benzoate), and sorbates (e.g., sodium sorbate, potassium sorbate, and calcium sorbate).

Exemplary antioxidants include, but are not limited to, vitamin C, vitamin E, or mixtures of natural tocopherols.

Exemplary buffering agents include, but are not limited to, citric acid, malic acid, tartaric acid, phosphoric acid, or their salts forms, that when used with other agents or compounds produces a stable pH between 6 and 8 and most preferably between 6.8 and 7.2.

Exemplary dispersing agents include, but are not limited to, polymer-based dispersing agents, such as polyvinylpyrrolidine (PVD); alkyhydroxy celluloses, such as hydroxypropylmethyl cellulose; various dextrins and cyclodextrins, such as hydroxypropyl-beta-cyclodextrin and hydroxypropyl-gamma-cyclodextrin; and all GRAS polyhydroxyalcohols.

Exemplary preservatives include, but are not limited to, ethylenediaminetetraacetic acid or one or more 4-hydroxy benzoic acid esters, such as methyl, ethyl, propyl and butyl analogs.

Exemplary solubilizing agents include, but are not limited to, polyhedric alcohols, such as polyethylene glycol with weights ranging between 200 and 1000 Da, and most preferably PEG 200, 400 and 600 alone or in combination with sorbitol, dipropylene glycol polyethylene, other glycol polyols, ethanol, and ethylenediaminetetraacetic acid (EDTA). Exemplary stabilizing agents include, but are not limited to, glycerin, pentaerythritol, or sodium alginate.

Exemplary surfactants include, but are not limited to, polyoxylglycerides, such as Labrafril®M 1944 CS (oleoyl macrogolglycerides), Labrafril®M 2125 CS (linoleoyl macrogolglycerides), Labrasol® (caprylocaproyl macrogolglycerides); caprylates, such as Capryol™ 90 (propylene glycol monocaprylate), and Capryol™ PGMC (propylene glycol caprylate); laurates, such as Lauroglycol™ 90 (propylene glycol monolaurate) and Lauroglycol™ FCC (propylene glycol laurate); oleates, such as Plurol® Oleique CC497 (polyglyceryl oleate); monoethyl ethers, such as Transcutol® HP (diethylene glycol monoethyl ether); sorbitan-based nonionic surfactants, such as Span® 20 (sorbitan monolaurate), Span® 80 (sorbitan oleate), and Span® 85 (sorbitan trioleate), including polyoxyethylene sorbitan-based surfactants, such as Tween® 60 (polysorbate 60) and Tween® 80 (polysorbate 80); emulsifier blends, such as Tandem® 552/522 K (mono-diglycerides and polysorbate 60) and Atmos® 300K (mono-diglycerides and propylene glycol); and tocopherol polyethyleneglycol 1000 succinate.

Exemplary viscosity controlling agents include gelatin, alginic acid, agarose, agar, carrageenan, gums (e.g., xanthan gum, locust bean gum, guar gum, tragacanth, gum karaya, and natural gum), and polysaccharides (e.g., methyl cellulose, glucomannan, galactomannan, and gulaman).

Exemplary vitamins include, but are not limited to, water-soluble vitamins (e.g., vitamins B1-5, 6, 7, 9, and 12 and C; and fat-soluble vitamins (e.g., vitamins A, D, E, or K).

For a patient with dysphagia, the viscosity of the solution or dispersion could be an important consideration. Patients with dysphagia typically require restriction of their diet to foods with appropriate viscosity. According to the National Dysphagia Diet, diets can include liquids or semi-solids that are categorized as being thin (1-50 cP), nectar-like (51-350 cP), honey-like (351-1750 cP), or spoon thick (>1751 cP) (The National Dysphagia Diet Task Force, The National Dysphagia Diet: Standardization for Optimal Care. Chicago, Ill., American Dietetic Association; 2002). The viscosity of the solution or dispersion herein can be any useful range (e.g., 1-450 cP, 1-1,000 cP, 1-2,000 cP, 1-200,000 cP, 50-1,000 cP, 50-2,000 cP, 500-100,000 cP, 1,000 to 200,000 cP, or 50,000 to 200,000 cP). In one example, the viscosity of the solution or dispersion is from 1 to 450 cP. In another example, the viscosity of the solution or dispersion is from 50,000 to 200,000 cP.

The compositions may optionally contain colorants, flavoring agents, sweeteners, or taste masking agents in order to provide a more palatable preparation. Exemplary colorants include titanium dioxide and dyes that can be found in Kirk Othmer Encyclopedia of Chemical Technology, Vol 5, Fourth edition, August 2009, pages 837-884. Exemplary flavoring agents include peppermint, menthol, orange, lemon, mint, cinnamon, cherry, lime, vanilla, tangerine, and, by incorporation, other flavorings described in National Academy of Sciences—National Research Council, "Chemicals Used in Food Processing," Publication 1274, pp. 63-258 (1965). Exemplary sweeteners include peptides of L-aspartylyphenylalanine methyl ester; water soluble sweeteners, including stevia saccharin salts (e.g., steviol glycosides, such as Rebiana, which contains mainly rebaudioside A), cyclamate salts, acefulfam-K, aspartame, sucralose, and glycyrrhizanates; natural sweeteners, including glucose, xylose, ribose, mannose, fructose, dextrose, sorbitol, and mannitol; and protein based sweeteners, such as thymidine and monellin. Exemplary taste masking agents include colloidal polysaccharides, including sodium alginate; and other taste masking agents, such as xanthum gum, carageenan, hydroxypropylmethyl cellulose, methyl cellulose, microcrystalline cellulose, and sodium carboxy methyl cellulose.

The method can include a number of post-processing steps. For example, the powdered composition can be further sterilized, such as by treatment with heat, an autoclave, or plasma oxidation; pulverized, such as by using a grinder or a mill; lyophilized.

Further modifications to the methods described herein can be include any method well-known in the pharmaceutical art, for example, as described in "Remington: The Science and Practice of Pharmacy" (20th ed., ed. A. R. Gennaro, 2000, Lippincott Williams & Wilkins).

The powdered composition can be characterized using various methods known to a skilled person in the arts. The characteristics of the powder within the powdered composition can be readily determined using any number of methods, including powder diffraction, light scattering, and microscopy (such as atomic force microscopy and scanning tunneling microscopy). The size of the powder can be determined by any useful method, including the determination of mesh size. The viscosity can be determined by any useful method, including a rheometer or a viscometer.

Furthermore, to determine the amount of pharmaceutically active compound bound to the peptide, the peptide may be digested from the compound to determine the exact composition by any useful method (e.g., HPLC method; mass spectrometry, such as electro spray mass spectrometry; or other analytical methods commonly employed by the pharmaceutical industry).

The concentration of one or more of the compounds in the formulation will vary depending on a number of factors, including the dosage of the drug to be administered, and the route of administration. Optimization of the appropriate dosages can readily be made by the skilled practitioner in light of the pharmacokinetics of the compound or combination of compounds used in the composition. Factors to be considered in setting dosages include the compound's specific activity; the severity of the condition or symptoms of the patient; the age, condition, body weight, sex, and diet of the patient; the use (or not) of concomitant therapies; and other clinical factors.

Administration may be one or multiple times daily, weekly (or at some other multiple day interval) or on an intermittent schedule, with that cycle repeated a given number of times (e.g., 2-10 cycles) or indefinitely. Alternatively, the compositions may be administered as symptoms occur.

The compositions are typically administered daily. In one embodiment, the composition comprises between 1% to 30% (w/w) of one or more compounds and 90% to 99% (w/w) of the protein. In another embodiment, the composition further comprises a protein or a hydrolyzed protein that is from 500 Da to 1,000,000 Da. In a preferred embodiment, the protein or hydrolyzed protein is more than 500 kDa.

The composition can include a pharmaceutically active compound and protein or a hydrolyzed protein useful weight ratio, such as from 1:1 to 1:1000 (e.g., 1:1, 1:2, 1:5, 1:10, 1:25, 1:50, 1:100, 1:500, 1:750, 1:1000, and other ratios therebetween). Preferable weight ratios include those from 1:10 to 1:100 (e.g., 1:10 to 1:20, 1:10 to 1:50, 1:20 to 1:100). These weight ratios can also be expressed as percentages, where the percentage of compound to protein would range between 1% and 10% by weight. Most commonly, the percentage of compound to protein would be in the range of 1-5%.

The ratio of the pharmaceutically active compound to the protein can also be expressed in terms of available binding sites of the protein. Typically, the available binding sites in the protein versus amount of compound are in great excess, where the range of excess binding sites may be in the range of 1,000 to greater than 10,000,000 (e.g., 5,000 to 10,000,000; 5,000 to 100,000,000; or 1,000 to 100,000,000).

Typically, the compositions of the invention are kept in the powder form until it is time to be administered to the patient, at which point the powder is mixed with a liquid carrier to form a stable liquid formulation. For example, the powdered composition can be admixed in any of a variety of liquids, such as water or milk, to form a liquid solution or dispersion (e.g. suspension, colloid, emulsion, etc.). In another example, the composition can be admixed in a semi-solid or soft food product, such as pudding or apple sauce.

The stability of the dispersion may readily be determined by a skilled person in the pharmaceutical or chemical arts. For example, the degradation products of the pharmaceutically active compound within the dispersion can be measured as a function of time. In another example, the sedimentation rate can be determined under equilibrium conditions.

Also provided herein are kits comprising the powdered composition. For example, the kits comprise a powdered composition, as described herein, a liquid, and instructions on admixing the powdered composition with the liquid. The kit can further include a container that can be used to admix the powdered composition with the liquid.

The liquid of the kit can be any aqueous solution, such as water or a buffer. The liquid can also include one or more of any of the agents described herein. Exemplary agents include a solubilizing agent, a stabilizing agent, a surfactant, a preservative, a taste masking agent, a sweetener, a flavoring agent, a dispersing agent, a colorant, a buffering agent, an absorption enhancing agent, an antioxidant, or a vitamin.

Proteins

As discussed above, the powdered compositions of the invention contain one or more pharmaceutically active compounds and a protein. The protein can be either a single well-characterized protein or a combination of proteins with similar molecular weights or varying molecular weights, such that acceptable and medically approved pharmacokinetic parameters are obtained.

Pharmacokinetic parameters may readily be determined by a skilled person in the arts. Pharmacokinetic (PK) analysis can be performed by non-compartmental (model independent) or compartmental methods. Non-compartmental methods estimate the exposure to a drug by estimating the area under the curve of a concentration-time graph. Compartmental methods estimate the concentration-time graph using kinetic models. Non-compartmental methods are often more versatile in that they do not assume any specific compartmental model and produce accurate results also acceptable for bioequivalence studies.

Non-compartmental PK analysis is highly dependent on estimation of total drug exposure. Total drug exposure is most often estimated by Area Under the Curve ("AUC") methods, with the trapezoidal rule (numerical differential equations) being the most common area estimation method. Due to the dependence on the length of 'x' in the trapezoidal rule, the area estimation is highly dependent on the blood/plasma sampling schedule. For example, the closer time points result in trapezoids that are more comparable to the actual shape of the concentration-time curve.

Compartmental PK analysis uses kinetic models to describe and predict the concentration-time curve. PK compartmental models are often similar to kinetic models used in other scientific disciplines, such as chemical kinetics and thermodynamics. The advantage of compartmental over some non-compartmental analyses is the ability to predict the concentration at any time. However, disadvantags include the difficulty in developing and validating the proper model. Compartment-free modeling based on curve stripping does not suffer this limitation. The simplest PK compartmental model is the one-compartmental PK model with intravenous bolus administration and first-order elimination. The most complicated PK models (called PBPK models) rely on the use of physiological information to ease development and validation.

The concentration-time profile can be constructed by any useful bioanalytic techniques, where proper bioanalytical methods should be selective and sensitive. Examples of such methods include chemical techniques to measure the concentration of drugs in a biological matrix (e.g., plasma); and mass spectrometry to observe low dose and long time point data in a biological matrix (e.g., blood or urine) with high sensitivity, such as LC-MS with a triple quadrupole mass spectrometer and/or tandem mass spectrometry.

Certain protein(s) may act as a drug class protein that binds an entire class of pharmaceutically active compounds. Examples of classes of pharmaceutically active compounds include statins, a class of lipid lowering agents that typically comprises a pharmacophore of a modified hydroxyglutaric acid component; dihydropyridines, a class of calcium channel blocking agents; angiotensin converting enzyme inhibitors, a class of molecules used to treat high blood pressure and heart failure; or certain types of protease inhibitors, a class of molecules used to treat AIDs related diseases.

A drug class protein can be determined using a variety of methods. For example, a certain protein can be chosen to bind a certain pharmacophore present in a class of pharmaceutically active compounds. As statins typically have a pharmacophore of a modified hydroxyglutaric acid component, a drug class protein could include positively charged amino acids that would form an ionic bond with the hydroxyglutaric acid component. Thus, each drug chemical class may have a specific drug class protein as a preferred binding partner in a complex.

However, specific drug class proteins are not always necessary. Proteins include those from any sources (e.g., natural or synthetic); those with multiple binding sites for cationic interactions, anionic interactions, or other neutral tight binding interactions; or those with pockets of lipophilic amino acids (e.g., glycine, alanine, valine, leucine, isoleucine, methionine, proline, phenylalanine, tyrosine, or tryptophan) or hydrophilic amino acids (e.g., serine, threonine, aspartic acid, glutamic acid, lysine, arginine, histidine, asparagine, or glutamine). For example, some proteins contain sites that allow for non-specific binding of all types of compounds. Preferably, the interaction between the protein and the therapeutic agent is a non-covalent interaction. Examples of such proteins include gelatin, casein, whey protein, albumin, and soy protein.

Proteins of particular interest to this method are gelatin, such as type A gelatin and type B gelatin. Examples of gelatin-based compositions include Jell-O®, which can be formed with varying viscosity. Another protein is whey protein, which can refer to one or more proteins found in whey, including alpha-lactalbumin, beta lactoglobulin, bovine serum albumin, glycomacropeptide (casein-derived protein), immunoglobulins (e.g., IgG1, IgG2, IgGA, and IgM), lactoferrin, and lactoperoxidase. Whey protein can also include other agents, such as lactose, calcium, or lipids (e.g., sphingolipids or conjugated linoleic acid). Whey may be further defined as a concentrate or isolate. Yet another particular protein is albumin, such as bovine serum albumin or human serum albumin. Albumin may be present as a concentrate or isolate. In addition, albumin may be supplied in any form, such as non-fat dried milk powder. Another protein of particular interest is soy protein, which can refer to one or more proteins found in soy, including β-congly-cinin (or a 7S form) or glycinin (a 11S form).

The composition can include any combination of one or more proteins or hydrolyzed proteins. For example, the composition includes both whey protein and casein, soy protein and casein, whey protein and albumin, or whey protein and soy protein.

For controlled release of the compound, casein could be used as the protein or as one of the proteins within a combination of proteins. Casein tends to form a gel within the stomach and can be used to release a compound slowly over time.

As described herein, the proteins can be hydrolyzed leading to smaller hydrolyzed protein with greater water solubility and greater specificity for a drug or drug class. A hydrolyzed protein includes any protein fragment that is shorter than a full length protein, such as fragment containing between 1% to 99% of the amino acids in the full length protein (e.g., between 10%-95%, 10%-75%, 10%-50%, 20%-95%, 20%-75%, 20%-50%, 30%-95%, 40%-95%, or 50%-95%). The smaller fragments will also be less likely to cause antigenic responses. In addition, hydrolyzed proteins are more likely to have water soluble dispersal characteristics. Furthermore, in some embodiments the protein may be denatured or partially denatured.

The protein or hydrolyzed protein can be of any useful size, such as from 500 to 10,000,000 Da (e.g., 500 Da to 100,000 Da, 500 Da to 500,000 Da, 500 Da to 10,000,000 Da, 1,000 Da to 100,000 Da, 1,000 Da to 500,000 Da, and 1,000 Da to 10,000,000 Da). In all cases, the size of the protein varies from a full length protein to a hydrolyzed protein. A hydrolyzed protein can be prepared by any method that breaks one or more peptide bonds (or amide bonds) in the full length protein. Peptide bonds can be broken by hydrolysis (e.g., treatment with one or more of an acid, base, heat, or bacterial extract in water or a buffer); by complete or limited proteolysis, such as by the use of enzymes (e.g., pepsin, trypsin, papain, bromelain, ficin, thermolysin, rennet, Alcalase®, Neutrase®, Protamex®, Novo-Pro™ D, or Flavourzyme®); or any combination thereof. The degree of hydrolysis can be determined by any method, such as column chromatography, molecular sieving, or direct sequencing of the peptide or hydrolyzed peptide.

Most commonly, hydrolyzed proteins are formed by partial enzymatic hydrolysis. Thus, the hydrolyzed protein may be fragments as small as 5 amino acids with a molecular weight as small as 500 Da. A most preferred size for the protein will be a size that allows for good solubilization in a solution or dispersion; or that will form a homogenous suspension in a solution or dispersion. The protein may vary in size based on solubility criteria and the overall charge surface density of the protein.

The protein may also be of a larger nature and be used as in a suspension (e.g., in a semi-solid food product). When larger proteins are used, these proteins may be hydrolyzed by using acidic conditions or by using heat. For example, heat or acidic conditions can be used for casein to determine which caseinate form will bind and trap the pharmaceutically active compound. When using casein, the composition will typically result in a slow release formulation of the compound. Thus, the nature of the protein can allow for quick release forms, which can be altered to produce slow release forms.

In addition to size, other physical characteristics of the protein can be considered. Ideally, the pharmaceutically active compound is tightly bound to the protein. The bond between the compound and the protein can be covalent and, more preferably, non-covalent (e.g., by an electrostatic bond, by van der Waals interactions, by virtue of multiple non-covalent binding regions, by lipophilic interaction, or by Log P-based attractions). In some cases, a specific compound having a free hydroxyl may be bound covalently to a free carboxyl function on the peptide, thereby forming an ester bond between the compound and the peptide. Eventually, the ester bond is hydrolyzed when the compound-protein complex is exposed to the acid environment of the stomach. In addition, the peptide will be digested in the stomach by gastric proteases and to some extent by intestinal proteases. This action will free the bound compound and allow for its normal absorption into the gastrointestinal tract.

Pharmaceutically Active Compounds

Suitable pharmaceutically active compounds or combinations thereof for use in the compositions and methods of the invention generally include those that are typically less than 500 Da. Suitable compounds include those in the contemporary editions of the Physician's Desk Reference (PDR), the Merck Manual, or a medical text book, Goodman and Gilman.

The compounds may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Examples of compounds or combinations thereof include:

$5-HT_{1A}$ receptor agonists (e.g., buspirone and tandospirone);

$5-HT_2$ receptor antagonists, such as $5-HT_{2A}$, $5-HT_{2B}$ and $5-HT_{2C}$ receptor antagonists (e.g., sarpogrelate, asenapine, clozapine, and olanzapine);

α-adrenergic receptor agonists (e.g., phenylephrine, pseudoephedrine, and oxymetazoline);

α-adrenergic receptor antagonists, also known as alpha-adrenoceptors or α-blockers (e.g., phenoxybenzamine, phentolamine, prazosin, and doxazosin);

β-adrenergic receptor agonists (e.g., salbutamol, albuterol, levalbuterol, terbutaline, bitolterol, salmeterol, formoterol, and bambuterol);

β-adrenergic receptor antagonists, also known as beta-adrenoceptors or β-blockers (e.g., carvedilol, propranolol, nadolol, timolol, pindolol, labetalol, metroprolol, atenalol, esmolol, and acebutolol);

acetylcholinesterase inhibitors (e.g., donepezil, galantamine, rivastigmine, and tacrine);

anesthetics (e.g., physostigmine, neostigmine, and procaine); angiotensin receptor antagonists (e.g., valsartan, losartan, olmesartan, and irbesartan);

angiotensin converting enzyme inhibitors (e.g., captopril, enalapril, lisinopril, and ramipril);

antibiotics, including penicillins (e.g., amoxicillin, ampicillin, and cloxicillin), cephalosporins (e.g., cefazolin, cefixime, ceftazidime, and ceftriaxone), polymixins, quinolones (e.g., ciprofloxacin, levofloxacin, moxifloxacin, gatifloxacin, and gemifloxacin), sulfonamides (e.g., sulfaisodimidine, sulfanilamides, sulfadiazine, sulfamethoxazole, sulfadimethoxine, and sulfamethoxypyridazine), glycopeptides (e.g., vancomycin), aminoglycosides (e.g., streptomycin, neomycin, spectinomycin, gentamicin, and kanamycin), macrolides (e.g., erythromycin, azithromycin, and ketolide), tetracyclines (e.g., doxycycline, chlortetracycline, mecycline, and tigecycline), cyclic lipopeptides (e.g., daptomycin), oxazolidinones (e.g., linezolid and torezolid), and combinations with other therapeutic agents (e.g., amoxicillin with clavulanate);

anticholinergic agents (e.g., ipratropium bromide, oxitropium bromide, and tiotropium);

anticoagulants (e.g., heparin, coumadin, enoxaparin, warfarin, apixaban, and rivaroxaban);

anticonvulsants (e.g., gabapentin, topiramate, hydantoin, benzodiazepines, zonisamide, valproic acid, ethosuximide, carbamazepine, primidone, lamotrigine, felbamate, levetiracetam, and tiagabine);

antidepressants (e.g., fluvoxamine, paroxetine, sertraline, desvenlafaxine, duloxetine, milnacipran, venlafaxine, bupropion, and atomoxetine);

antidiabetic agents (e.g., insulin, metformin, glipizide, glyburide, glimepiride, gliclazide, repaglinide, nateglinide, rosiglitazone, pioglitazone, miglitol, acarbose, liraglutide, vildagliptin, and sitagliptin);

antifungal agents (e.g., clotrimazole, ciclopirox, ketoconazole, itraconazole, fluconazole, abafungin, terbinafine hydrochloride, amorolfine, naftifine, and butenafine);

antiinflammatory agents (e.g., aspirin, diclofenac, and cyclooxygenase inhibitors, such as ibuprofen, ketoprofen, and naproxen);

antihistamines (e.g., carbinoxamine, clemastine, dimenhydrinate, pyrilamine, tripelennamine, chlorpheniramine, brompheniramine, hydroxyzine, cyclizine, acrivastine, cetririzine, azelastine, loratadine, fexofenadine, doxepin, diphenhydramine, and all tricyclics that have antihistaminic activity, such as amitriptyline, imipramine, promethazine, chlorpromazine, and nortriptyline);

antipsychotic agents (e.g., 5-HT$_{2A}$ receptor antagonists, dopamine antagonists, haloperidol, droperidol, chlorpromazine, fluphenazine, perphenazine, prochlorperazine, thioridazine, aripiprazole, trifluoperazine, mesoridazine, periciazine, promazine, triflupromazine, promethazine, chlorprothixene, flupenthixol, thiothixene, zuclopenthixol, clozapine, olanzapine, risperidone, quetiapine, ziprasidone, and zotepine);

antiplatelet agents (e.g., abciximab, eptifibatide, tirofiban, clopidogrel, ticlopidine, prasugrel, beraprost, prostacyclin, iloprost, treprostinil, aspirin, ditazole, cloricromen, dipyridamole, and triflusal);

antithrombotic agents (e.g., aspirin, dipyridamole, clopidogrel, prasugel, and cangrelor);

antiviral agents, including DNA antivirals (e.g., acyclovir, valaciclovir, ganciclovir, famciclovir, vidarabine, foscarnet, tromantadine, rifampicin, entecavir, lamivudine, telbivudine, adefovir, stavudine, zidovudine, abacavir, and tenofovir), general nucleic acid inhibitors (e.g., cidofovir, interferon alfa-2b, peginterferon alfa-2a, ribavirin, and taribavirin), and RNA antivirals (e.g., boceprevir, telaprevir, pleconaril, arbidol, amantadine, rimantadine, oseltamivir, zanamivir, peramivir, and laninamivir);

anxiolytic agents (e.g., alprazolam, chlordiazepoxide, clonazepam, diazepam, lorazepam, benzodiazepines, and 5-HT$_{1A}$ receptor agonists);

cholesterol-lowering drugs, such as statins (e.g., atorvastatin, pravastatin, simvastatin, and rusovastatin);

dopamine agonists (e.g., apomorphine, bromocriptine, cabergoline, lisuride, pergolide, piribedil, pramipexole, and ropinirole);

dopamine antagonists (e.g., amisulpride and sertindole);

eicosanoid inhibitors (e.g., zafirlukast, zileuton, and montelukast);

glucocorticoids (e.g., beclomethasone, hydrocortisone, cortisone acetate, prednisone, prednisolone, methylprednisolone, dexamethasone, betamethasone, triamcinolone, fludrocortisone acetate, deoxycorticosterone acetate, and aldosterone);

ion channel blocking agents, such as calcium channel blockers (e.g., nifedipine, amlodipine, felodipine, flunarizine, diltiazem, verapamil, nifedipine, and nimodipine) or sodium channel blockers (e.g., procainamide, quinidine, ajmaline, disopyramide, prajmaline, sparteine, lidocaine, mexiletine, tocainide, aprindine, encainide, flecainide, lorcainide, moricizine, and propafenone);

monoamine oxidase B inhibitors (e.g., selegiline and rasagiline);

N-methyl d-aspartate (NMDA) receptor antagonist (e.g., dextromethorphan and memantine);

norepinephrine reuptake inhibitor (e.g., reboxetine, duloxetine, and amitriptyline);

opioids (e.g., morphine, codeine, meperidine, and oxycodone);

prostaglandins (e.g., epoprostenol and alprostadil);

proton pump inhibitors (e.g., omeprazole, esomeprazole, pantoprazole, lansoprazole, and rabeprazole);

renin antagonist (e.g., aliskiren and antidepressants with renin antagonistic activity, such as citalopram, escitalopram, and fluoxetine);

serotonergics (e.g., a selective serotonin reuptake inhibitor, a serotonin agonist, and a serotonin partial agonist);

steroidal anti-inflammatory agents (e.g., hydrocortisone, cortisone acetate, fludrocortisone acetate, deoxycorticosterone acetate, prednisone, prednisolone, methylprednisolone, dexamethasone, betamethasone, triamcinolone, beclometasone, and aldosterone);

tricyclics (e.g., amitriptyline and imipramine);

thromboxane A2 agonists (e.g., ramatroban and seratrodast); and triptans (e.g., almotriptan, eletriptan, frovatriptan, naratriptan, rizatriptan, sumatriptan, and zolmitriptan);

vasodilators (e.g., glyceryl trinitrate, isosorbide dinitrate, isosorbide mononitrate, linsidomine, molsidoymine, pentaerythritol tetranitrate, and flosequinan); and miscellaneous drugs, such as pentoxifylline and cilostazol.

Particularly favored compounds or combinations thereof include those generally taken by the elderly or by those with dysphagia. Examples of compounds taken by the elderly include drugs for the treatment of CNS disorders, such as Parkinson's Disease, Alzheimer's Disease, dementia, Huntington's Chorea, and endogenous depression; cardiovascular disease, such as congestive heart failure, peripheral artery disease, arrhythmias, and hypertension; pulmonary diseases, such as asthma and chronic obstructive disease; infections of a viral bacterial or fungal nature; gastrointestinal diseases, such as gall bladder disease, diverticulolitis, irritable bowel disease, gastroesophageal reflux, and gastric and intestinal ulcers; urinary disease, such as urinary incontinence, women's health issues, such an osteoarthritic condition; men's health issues, such as benign prostate hyperplasia; cancers, such as head and neck, lung, breast, and colon; and endocrine disorders associated with pituitary and adrenal function.

The pharmaceutically active compounds include any type of compound or combinations thereof to treat one or more common diseases of different or same etiology. These compounds and combinations include compounds to treat CNS disorders; one or more drugs to treat cardiovascular disease; one or more drugs to treat pain and inflammation; one or more drugs to treat gastrointestinal disease; one or more antibiotics, antiviral agents or antifungal agents to treat infections; or one or more compounds to treat complex multiple independent disease states.

Examples of compounds to treat CNS disorders (e.g., Alzheimer's disease, dementia, and Parkinson's disease) include acetylcholinesterase inhibitors, NMDA receptor antagonists, antipsychotic agents, anxiolytic agents, levodopa, dopamine agonists, monoamine oxidase B inhibitors; compounds to treat pulmonary diseases (e.g., asthma) include β-adrenergic receptor agonists, anticholinergic agents, eicosanoid inhibitors, and inhaled or oral glucocorticoids; compounds to treat cardiovascular disease (e.g., heart failure) include β-adrenergic receptor antagonists, acetylcholinesterase inhibitors, angiotensin receptor antagonists, and vasodilators; compounds to treat pain and inflammation include antiinflammatory agents, anesthetics, and opioids; compounds to treat gastrointestinal diseases (e.g., irritable bowel disease, gastroesophageal reflux, or gastric and intestinal ulcers) include serotonergics, tricyclics, anticholinergic agents, opiates, proton pump inhibitors, and $H_2$ receptor antagonist (e.g., cimetidine); and compounds to treat vascular diseases include antithrombotic agents, anticoagulants, cholesterol-lowering drugs, or antiplatelet agents, where examples of these compounds are provided herein.

Other suitable compounds or combinations thereof include those taken frequently, for example, at least once a day. Examples of such compounds include an alpha adrenoceptor agonist (e.g., phenylephrine or pseudoephedrine); an analgesic (e.g., physostigmine, neostigmine, or procaine); an anesthetic; an anticonvulsant (e.g., gabapentin); an anticholinergic compound; an antihistamine (e.g., diphenhydramine); an antiinflammatory compound, such as a nonsteroidal antiinflammatory drug; a beta 2 receptor antagonist (e.g., propranolol); a cyclooxygenase inhibitor (e.g. ibuprofen, ketoprofen, or naproxen); an ion channel blocking compound, such as a sodium channel blocker or a calcium channel blocker; a N-methyl d-aspartate (NMDA) receptor antagonist (e.g., dextromethorphan); a norepinephrine reuptake inhibitor; a selective serotonin reuptake inhibitor; a serotonin agonist; a serotonin partial agonist; a tricyclic (e.g., amitriptyline or imipramine); and/or a triptan (e.g., almotriptan, eletriptan, frovatriptan, naratriptan, rizatriptan, sumatriptan, or zolmitriptan).

Combinations of two or more compounds can be administered to a patient. Exemplary combinations include a combination of compounds for the treatment of heart failure or vascular disease; two antibiotics; or two compounds for the treatment of mixed therapeutic needs, such as hypertension and heart failure or asthma and vascular disease.

Pharmaceutically active compounds also encompass any nutraceutical and combinations of substances that have therapeutic or preventative health purposes. Examples of nutraceuticals include niacin, carnitine, acetylcarnitine, co-enzyme Q-10, policosanol, vitamins, and natural antioxidants, such as lipoic acid, vitamin E, and vitamin C Further features and advantages of this invention are further illustrated by the following examples, which are in no way intended to be limiting thereof.

EXAMPLES

Example 1

General Preparation of Liquid Formulation

In a vessel, a protein with water-soluble dispersal characteristics, such as a hydrolyzed whey protein, was brought into a solution or a suspension with an aqueous solvent, such as water or a buffer. A concentrate of drug was then prepared, using standard and specific and known methods, to bring the drug into solution. The protein solution was warmed to approximately 37° C. and the drug concentrate is slowly added with constant stirring. The drug was allowed to bind to equilibrium with the protein. The protein was in far excess to the drug product, thus driving the drug product to be largely bound at equilibrium. Typically, the available binding sites in the protein versus amount of drug to be bound are in great excess, where the range of excess binding sites may be in the range of 1,000 to greater than of 10,000,000. In terms of weight considerations, the percent drug to protein would range between 1% and 10% by weight. Most commonly, drug product to protein product would be in the range of 1-5%. After achieving equilibrium, the protein:drug complex was cooled to minimally room temperature or 23° C., filtered, and resuspended in an aqueous solution. Colorants, preservatives, taste masking agents, and other agents can be added to the aqueous solution to induce optimal viscosity.

Example 2

Fentanyl Binding to Bovine Serum Albumin (BSA) as Measured by Equilibrium Dialysis A standard two-compartment equilibrium dialysis method was used to measure the binding of fentanyl to BSA. In compartment "A" was placed a 0.78 mM fentanyl solution and 95 mg/ml BSA in a 25 mM phosphate buffer at pH 7. In compartment "B" was placed a 25 mM phosphate buffer at pH 7. Compartments A and B were allowed to come to equilibrium over a four-day period at room temperature. Fentanyl concentrations were measured after diluting samples 1/10,000 using an Agilent 6460 triple quadrupole mass spectrometer (Agilent Technologies, Santa Clara, Calif., USA) using the following protocol, and the results are reported in Table 3 below:

Sample Preparation.

Plasma samples (50 µL) were mixed with acetone containing 1% pyridine (200 µL) in a pre-tared centrifuge tube. All samples were centrifuged at 4° C. for 10 minutes, 15,000 rpm. After recording sample weights, supernatants were transferred to a second pre-tared centrifuge tube and the volume was reduced in vacuo by use of a SpeedVac concentrator. The residual acetone-free sample volumes were determined by weight. The average sample volumes following concentration were approximately 40 µL.

Analysis by LC-MS/MS.

A 5 µL aliquot of each processed sample was subjected to liquid chromatography on a 1200 series Agilent liquid chromatograph interfaced with an Agilent 6460 Triple Quad LC/MS. The chromatographic conditions are summarized in Table 1. Detection of either fentanyl or ketoprofen was by MRM. The precursor ion for fentanyl was 337 m/z and product ions were 188 and 105 m/z (m+1). The precursor ion for ketoprofen was 255 m/z and product ions were 209 and 105 m/z (m+1). The mass spectroscopic conditions are summarized in Table 2.

TABLE 1

HPLC Assay Conditions

| | |
|---|---|
| Injection Volume | 5 μl |
| Run Time | 4 min |
| Mobile Phases | "A" 0.1% formic acid in water |
| | "B" 0.1% formic acid in acetonitrile |
| Gradient | 0-0.5 min 2% "B" |
| | 0.51-2.5 min 70% "B" |
| | 2.51-4 min 2% "B" |
| Flow Rate | 0.8 ml/min |
| Column | Agilent Zorbax Eclipse XDB-C18 Rapid Resolution HT, 4.6 × 50 mm, 1.8 micron, 600 Bar, PN 927975-902 |
| Column Temp. | 60° C. |

TABLE 2

Mass Spectroscopic Conditions

| | |
|---|---|
| Ion Source | ESI + Agilent Jet Stream |
| Scan Type | MRM |
| Polarity | Positive |
| Scan Segments | Fentanyl |
| | Prec Ion 337.2 Prod Ion 188.1 Frag |
| | 136 V CE 18 V (Qual Prod 105, CE 38 V) |
| | Ketoprofen |
| | Prec Ion 255 Prod Ion 104.9 Frag |
| | 100 CE 10 (Qual Prod 209, CE 20) |
| Gas Temp | 300° C. |
| Gas Flow | 5 l/min |
| Nebulizer | 45 psi |
| Sheath Gas Temp | 250° C. |
| Sheath Gas Flow | 11 l/min |
| Capillary | 3500 V |
| Nozzle Voltage | 500 V |

The results, provided in Table 3 below, indicated that following three separate determinations, Fentanyl was shown to bind to BSA protein.

TABLE 3

Fentanyl Binding to BSA Protein

| Sample | Compartment | Fentanyl (μM) | BSA (mg/ml) | Binding Preference A/B |
|---|---|---|---|---|
| Control (no BSA) | A | 391 | 95 | 0.95 |
| | B | 410 | 0 | |
| Determination 1 | A | 544 | 95 | 4.0 |
| | B | 136 | 0 | |
| Determination 2 | A | 639 | 95 | 4.4 |
| | B | 145 | 0 | |
| Determination 3 | A | 552 | 95 | 2.45 |
| | B | 225 | 0 | |

Example 3

Antinociception (Analgesia) in Mice Given Fentanyl Formulated in Water or Bound to BSA Mice weighing on average 32 grams were gavaged p.o. (orally) with fentanyl prepared either in a water solution or following binding to BSA. Equimolar amounts of fentanyl base were used in each formulation. Analgesia was assessed by tail withdrawal reflex using a water stimulus at 55° C. The results are provided in FIGS. 1A, 1B and 2.

Figure 1B:
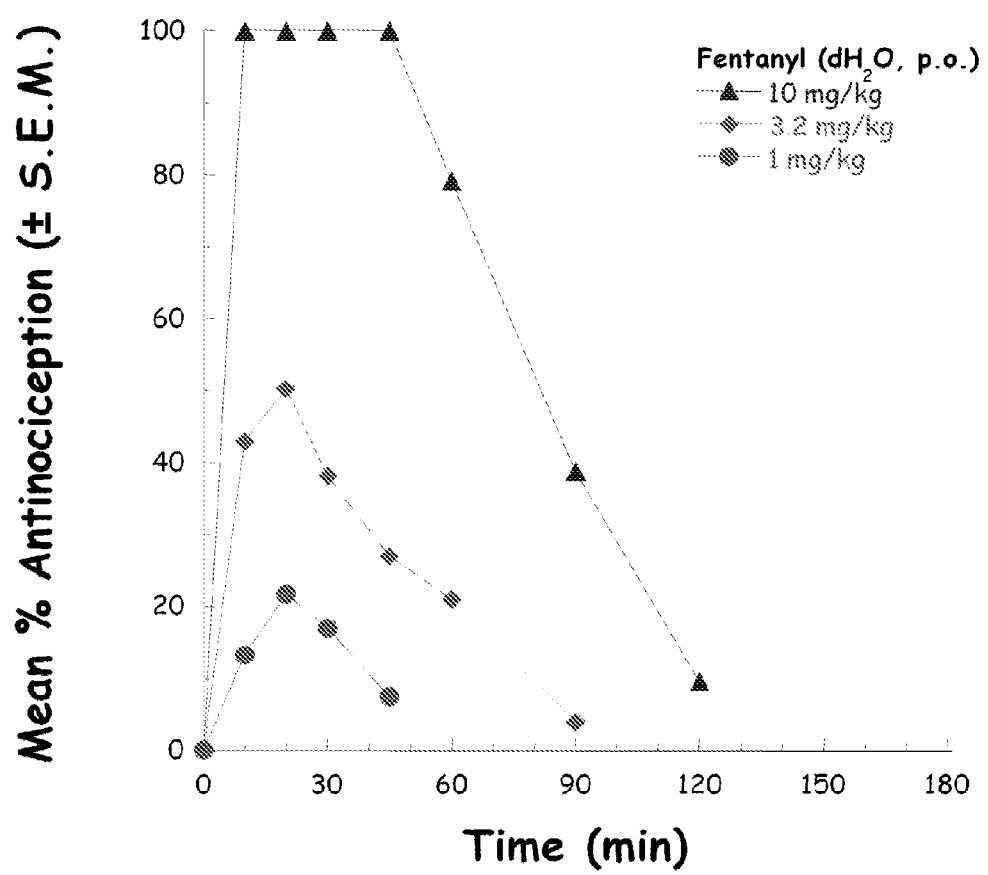
FIG. 1B is a graph showing antinociception over time in mice treated with 10 mg/kg, 3.2 mg/kg, or 1 mg/kg fentanyl formulated in a bound state with Bovine Serum Albumin (BSA).
Figure 2:
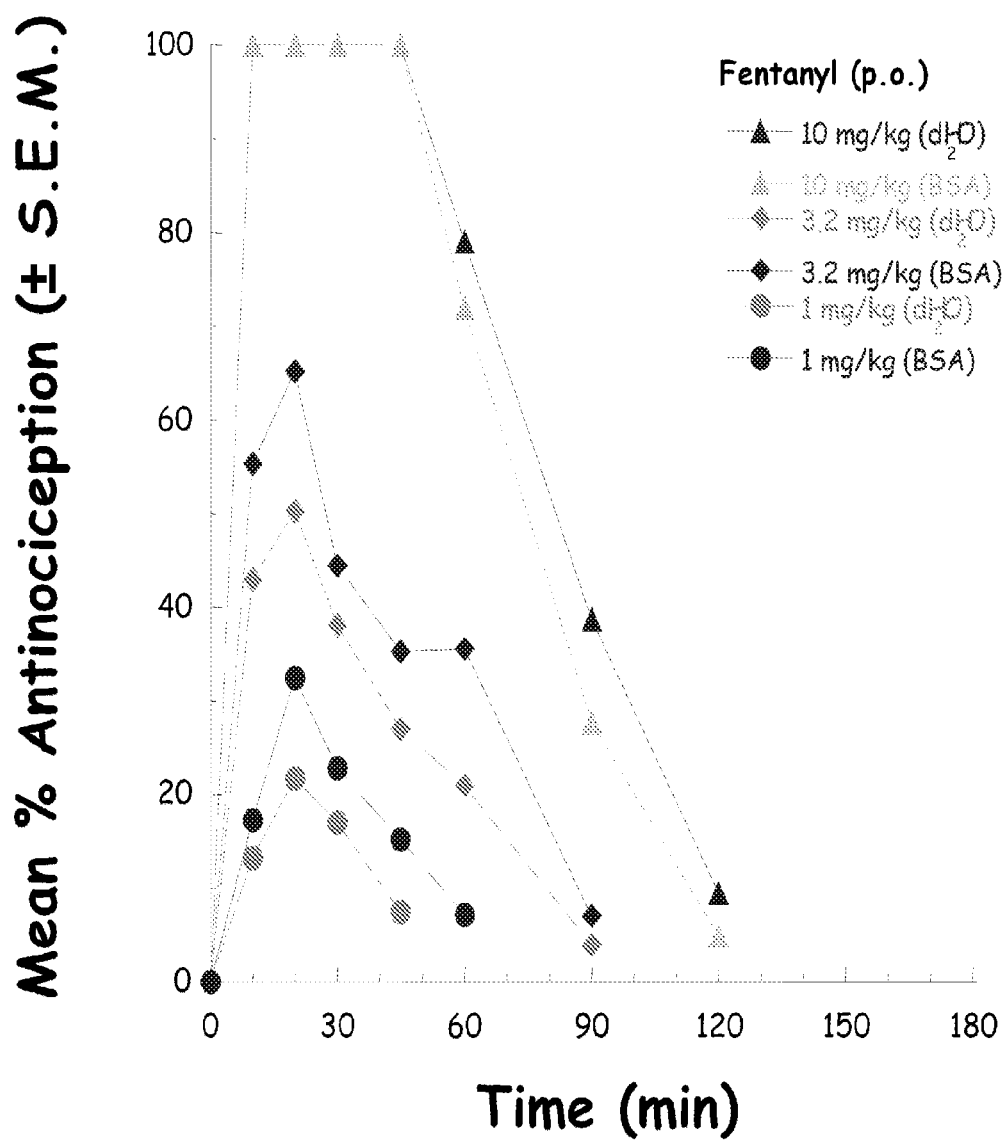
FIG. 2 is a graph comparing the antinociception over time in mice treated with fentanyl formulated in water versus fentanyl bound to BSA. The data show that fentanyl bound to BSA produced a greater analgesic response than fentanyl formulated in water (compare the results for 1 mg/kg and 3.2 mg/kg fentanyl in water vs. the BSA formulation).

The data provided in FIGS. 1A and 1B demonstrate that both fentanyl formulated in water or formulated in a bound state to BSA is equally potent to induce analgesia in a dose response relationship (each data point provided in FIGS. 1A and 1B represents three separate determinations). FIG. 2 presents a direct comparison of fentanyl formulated in water with fentanyl bound to BSA (as provided in FIGS. 1A and 1B). In these experiments, fentanyl bound to BSA produced a larger analgesic response (see data for 1 and 3.2 mg/kg fentanyl in water as compared to the BSA formulation).

Example 4

Ketoprofen Binding to Bovine Serum Albumin (BSA) as Measured by Equilibrium Dialysis A standard two-compartment equilibrium dialysis method was used to measure ketoprofen binding to BSA. In compartment "A" was placed a 0.608 mM solution of ketoprofen with 143 mg/ml BSA in 0.9% NaCl. In compartment "B" was placed 0.9% NaCl. Compartments A and B were allowed to come to equilibrium over a three-day period at room temperature. Ketoprofen concentrations were measured after diluting samples 1/1,000 using an Agilent 6460 triple quadrupole mass spectrometer (Agilent Technologies, Santa Clara, Calif., USA) (see protocol described above). The results for four determinations are provided in Table 4 below.

TABLE 4

Ketoprofen Binding to BSA Protein

| Sample | Compartment | Ketoprofen (μM) | BSA (mg/ml) | Binding Preference A/B |
|---|---|---|---|---|
| Control (no BSA) | A | 280 | 0 | No Binding |
| | B | 325 | 0 | |
| Determination 1 | A | 515 | 143 | 100% Bound |
| | B | 0 | 0 | |
| Determination 2 | A | 696 | 143 | 100% Bound |
| | B | 0 | 0 | |
| Determination 3 | A | 481 | 143 | 100% Bound |
| | B | 0 | 0 | |
| Determination 4 | A | 532 | 143 | 100% Bound |
| | B | 0 | 0 | |

Example 5

Comparison of Pharmacokinetic Absorption Profile for Ketoprofen Formulated in 0.9% NaCl Vs. Ketoprofen Bound to BSA Solution Mice weighing on average 32 grams were gavaged with 1, 3.2, or 10 mg/kg ketoprofen formulated in either 0.9% NaCl or bound to BSA at 143 mg/ml. At 30 minutes post-ketoprofen dosing, mice were anesthetized with isoflurane, the chest was opened and blood was taken by cardiac puncture from the left ventricle using a 1 ml syringe (22G 1 inch needle).

Figure 3:
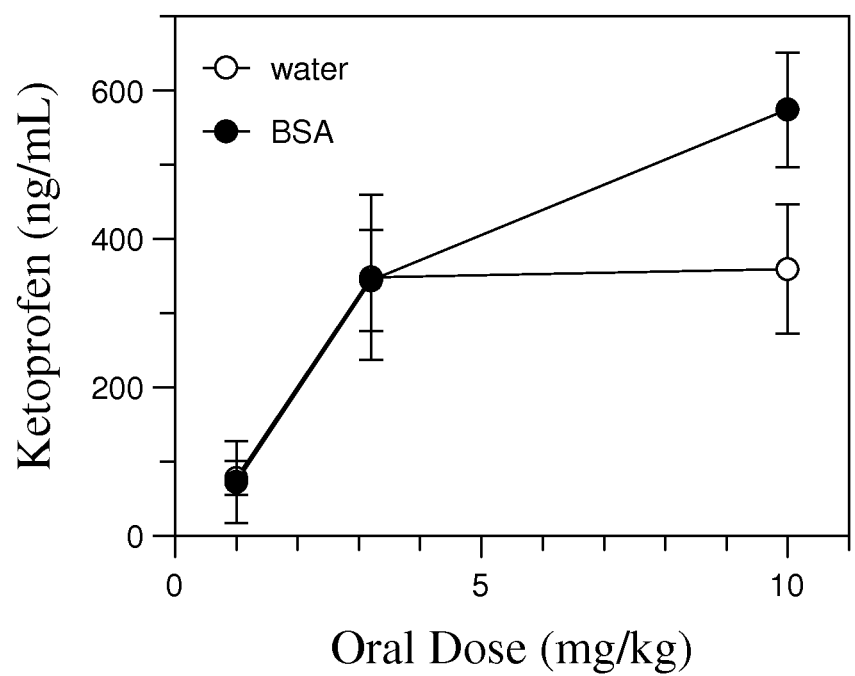
FIG. 3 is a graph showing the absorption profile for ketoprofen administered in saline or bound to BSA.

Blood was placed in 1 ml of EDTA treated microcontainers and stored on ice. Plasma separated from whole blood using a 1500 rpm spin for 15 minutes. Free plasma was stored on ice and analyzed for the presence of ketoprofen using a Agilent 6460 triple quadrupole mass spectrometer (Agilent Technologies, Santa Clara, Calif., USA). The absorption profiles for ketoprofen administered in saline and for ketoprofen bound to BSA were determined and are provided in FIG. 3. Each data point is the average of three separate determinations. At 1 mg/kg and 3.2 mg/kg there was no difference between the absorption of ketoprofen bound to BSA versus ketoprofen administered in saline. The data for high dose ketoprofen (10 mg/kg) indicate that BSA facilitates the absorption of ketoprofen and may increase the bioavailability of the drug.

All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, pharmacology, or related fields are intended to be within the scope of the invention.

What is claimed is:

1. A method of administering a pharmaceutically active compound to a patient in need thereof, the method comprising the steps of:
    (a) providing a powdered composition comprising (i) an effective amount of a pharmaceutically active compound and (ii) a protein, wherein the protein is bovine serum albumin or human serum albumin, and wherein the pharmaceutically active compound is 1% to 30% (w/w) of the powdered composition, and the protein is 70% to 99% (w/w) of the powdered composition;
    (b) mixing the powdered composition with a liquid, wherein the liquid is water or an aqueous solution, to form a liquid formulation that is a stable solution or dispersion; and
    (c) orally administering the solution or dispersion to the patient;
    wherein said pharmaceutically active compound is omeprazole, esomeprazole, atorvastatin, pioglitazone, donepezil, olanzapine, nifedipine, metoprolol, valsartan, prednisone, amlodipine, or lansoprazole.

2. The method of claim 1, wherein the protein is digested in the stomach by gastric proteases or intestinal proteases thereby releasing the compound for absorption into the gastrointestinal tract when the solution is orally administered.

3. The method of claim 1, wherein the size of the powder is from 1 to 100 mesh.

4. The method of claim 1, wherein the viscosity of the dispersion is from 1 cP to 450 cP.

5. The method of claim 1, wherein the viscosity of the dispersion is from 50,000 cP to 200,000 cP.

6. The method of claim 1, wherein the composition further comprises one or more agents selected from the group consisting of an absorption enhancing agent, an antimicrobial, an antioxidant, a buffering agent, a colorant, a dispersing agent, a flavoring agent, a preservative, a solubilizing agent, a stabilizing agent, a surfactant, a sweetener, a taste masking agent, a viscosity controlling agent, and a vitamin.

7. The method of claim 6, wherein the agent is the absorption enhancing agent selected from the group consisting of achitosan, type A gelatin, and type B gelatin.

8. The method of claim 6, wherein the agent is the antimicrobial selected from the group consisting of methylparaben, propylparaben, sodium benzoate, propyl benzoate, sodium sorbate, potassium sorbate, and calcium sorbate.

9. The method of claim 6, wherein the agent is the buffering agent selected from the group consisting of citric acid, malic acid, tartaric acid, phosphoric acid, and pharmaceutically acceptable salts thereof.

10. The method of claim 9, wherein the amount of the buffering agent results in the dispersion having a pH from 6 to 8.

11. The method of claim 10, wherein the pH is from 6.8 to 7.2.

12. The method of claim 6, wherein the agent is the dispersing agent selected from the group consisting of a polyvinylpyrrolidine, an alkyhydroxy cellulose, a dextrin, a cyclodextrin, and a polyhydroxyalcohol.

13. The method of claim 6, wherein the agent is the preservative selected from the group consisting of ethylenediaminetetraacetic acid and a 4-hydroxy benzoic ester.

14. The method of claim 6, wherein the agent is the solubilizing agent selected from the group consisting of 200 Da to 1000 Da polyethylene glycol, sorbitol, a glycol polyol, and dipropylene glycol polyethylene.

15. The method of claim 6, wherein the agent is the stabilizing agent selected from the group consisting of glycerin, pentaerythritol, and sodium alginate.

16. The method of claim 6, wherein the agent is the surfactant selected from the group consisting of a polyoxylglyceride, a caprylate, a laurate, an oleate, a monoethyl ether, a sorbitan-based nonionic surfactant, a polyoxyethylene sorbitan-based surfactant, an emulsifier blend, and tocopherol polyethyleneglycol 1000 succinate.

17. The method of claim 6, wherein the agent is the sweetener selected from the group consisting of an L-aspartylyphenylalanine methyl ester, a stevia saccharin salt, a cyclamate salt, acefulfam-K, aspartame, sucralose, a glycyrrhizanate, glucose, xylose, ribose, mannose, fructose, dextrose, sorbitol, mannitol, thymidine, and monellin.

18. The method of claim 6, wherein the agent is the taste masking agent selected from the group consisting of sodium alginate, xanthum gum, carageenan, hydroxypropylmethyl cellulose, methyl cellulose, microcrystalline cellulose, or sodium carboxy methyl cellulose.

19. The method of claim 6, wherein the agent is the viscosity controlling agent selected from the group consisting of gelatin, alginic acid, agarose, agar, carrageenan, xanthan gum, locust bean gum, guar gum, tragacanth, gum karaya, natural gum, methyl cellulose, glucomannan, galactomannan, and gulaman.

20. The method of claim 1, wherein the powdered composition is prepared by:
    (a) dispersing the protein in water or an aqueous solution at a first temperature ranging from 20° C. to 25° C. to form a protein mixture;
    (b) adding an effective amount of the pharmaceutically active compound to the protein mixture;
    (c) before or after the compound has been added to the protein mixture, heating the protein mixture to a second temperature ranging from 25° C. to 37° C., wherein the amount of the protein is in excess of the effective amount of the compound;
    (d) cooling the mixture to a third temperature ranging from 5° C. to 23° C.; and
    (e) separating or lyophilizing the mixture from the aqueous solution to obtain the powdered composition.

21. The method of claim 1, wherein the patient is suffering from dysphagia.

22. The method of claim 1, wherein the viscosity of the dispersion is from 1 cP to 200,000 cP.

23. The method of claim 1, wherein the pharmaceutically active compound is pioglitazone, omeprazole, esomeprazole, lansoprazole, atorvastatin, or metroprolol.

24. The method of claim 23, wherein the pharmaceutically active compound is pioglitazone, omeprazole, or atorvastatin.

* * * * *